United States Patent [19]
Fenyö et al.

[11] Patent Number: 4,686,986
[45] Date of Patent: Aug. 18, 1987

[54] METHOD AND APPARATUS FOR PROMOTING HEALING

[76] Inventors: Marta Fenyö, H-1094 Tompa u. 12.; Iván Kertész, H-1121 Költö u. 2-4; Károly Rózsa, H-1115 Szakasits Áu. 44B; Péter Szegö, H-1022 Hankóczy J.u. 27/A, all of, Budapest, Hungary

[21] Appl. No.: 371,954

[22] Filed: Apr. 26, 1982

[30] Foreign Application Priority Data

Sep. 2, 1981 [HU] Hungary ............................. 2538/81
Feb. 23, 1982 [HU] Hungary ............................ 04016/82

[51] Int. Cl.⁴ ................................................. A61N 5/00
[52] U.S. Cl. ........................... 128/396; 250/504 R; 350/394
[58] Field of Search ................... 128/395–398; 250/503.1, 504 R, 225; 350/394

[56] References Cited

U.S. PATENT DOCUMENTS

| | | | |
|---|---|---|---|
| 3,127,513 | 3/1964 | Rupprecht | 250/504 |
| 3,510,198 | 5/1970 | Pace | 350/394 X |
| 3,648,706 | 3/1972 | Holzer | 128/395 |
| 3,778,619 | 12/1973 | Carnel | 250/225 |
| 4,298,005 | 11/1981 | Mutzhas | 128/396 |

FOREIGN PATENT DOCUMENTS

| | | | |
|---|---|---|---|
| 0023311 | 2/1981 | European Pat. Off. | 128/306 |
| 2717233 | 11/1978 | Fed. Rep. of Germany | |
| 319869 | 10/1929 | United Kingdom | 350/394 |
| 603393 | 4/1978 | U.S.S.R. | 128/395 |

OTHER PUBLICATIONS

Mester et al., "Effects of Direct Laser Radiation . . . ", Arch Derm. Research, 263, 241–245, 1978.
Greguss, "A Model of Nonthermal Laser Effects . . . ", Laser 77 Opto–Electronics Conf. Proc., Munich. 1977.

*Primary Examiner*—Lee S. Cohen
*Attorney, Agent, or Firm*—McGlew and Tuttle

[57] ABSTRACT

A method and apparatus for the stimulation of biological processes related to cellular activity, particularly for promoting the healing of lesions on the body-surface, i.e. wounds, ulcers and epithelial injuries.

The lesion is irradiated with linearly polarized light of predetermined intensity, comprising incoherent components of wavelength, exceeding 300 nm.

The apparatus comprises a light source, constituted by a lamp emitting incoherent visible and/or infrared light, a deflecting system projecting the light beams into the given direction of treatment, a polarizer placed in the path of the light beam, projected into the direction of treatment, and preferably ultraviolet and infrared filters.

21 Claims, 32 Drawing Figures

METHOD AND APPARATUS FOR PROMOTING HEALING

FIELD AND BACKGROUND OF THE INVENTION

A method and apparatus for the stimulation of biological processes related to cellular activity, particularly for promoting the healing of lesions on the body surface i.e. wounds, ulcers and various epithelial injuries.

The invention relates to a method and apparatus for the stimulation of biological processes related to cellular activity, particularly for promoting the healing of lesions on the body-surface i.e. wounds, ulcers and various epithelial injuries, which is based upon the use of the biostimulating effect of light.

The irradiation of a living surface with laser light has, as it is widely known, a biostimulating effect. The experiments in this field have been conducted since 1967 under the guidance of professor Endre Mester and the initially modest presumptions have been broadly proven since that time. The healing effect of the treatment with laser light has already a very broad literature. The summary of experiences is included among other publications e.g. in the work of professor Endre Mester: "Laser Application in Promoting of Wound-Healing", published in the 1980 issue of the "Laser in Medicine" (edited by H. K. Koebner, Wiley-Interscience Publ. 1980.). Another work by professor Endre Mester: "Der Laser" can also be regarded as a summary of his experiences (edited by K. Dinstl and P. L. Fischer, Springer-Verlag, 1981.). It should be noted that in contrast to the laser light, no other treatments carried out by natural or artificial light have manifested any biostimulating effect thus far.

The healing effect of the laser light becomes apparent mainly in the healing of refractory wounds and ulcers. It is well known that such lingering ulcers develop fairly frequently on aged people suffering from cardiovascular troubles. Refractory bed-sores also tend to develop as a consequence of prolonged decubitus.

In the course of treatment with laser light, the laser light is directed onto the wound by means of a prism, a mirror or a fibre-optic and the entire surface of the wound is scanned by the correspondingly deflected beam. The specific intensity of the beam is between 20–150 mW/cm$^2$, and the maximum energy density is set to be about 4 J/cm$^2$. The treatment is usually recurrent, performed generally twice a week and the average time of healing is estimated to be about 10–12 weeks.

There are a great number of mutually contradictory theories, attempting to explain the biostimulating effect of the laser light, however, none of these could provide a scientifically acceptable explanation.

On the basis of the published results laser light would have a wide field of application, however, practical experiences show that it did not come into general use to an extent which it would deserve by its efficiency.

There are several reasons that slow down the wide scale acceptance of this treatment, one of which might be that the design of continuously operating lasers providing the required output and beam diameter is rather complicated and besides the sophisticated technical environment they also require special skills during manufacture.

SUMMARY OF THE INVENTION

The object of the invention is to provide a method and an apparatus that can establish a biostimulating effect, at least equivalent to that of the laser light, without the technical difficulties connected with the generation of laser light.

For solving this task it has been considered as a starting point that in its physiological state, the lipid bilayer of the cell membrane is in a phase similar to that of liquid crystals. It is known from the interaction between polarized light and liquid crystals, that over a certain intensity threshold polarized light can induce a change of state in liquid crystals. It has been assumed that polarized light of certain properties can reorder the polar heads of the lipid bilayer of the cell membrane or it can induce such a reordering process. It has also been expected that such an internal re-arrangement would bring about a noticeable change in the cellular processes related to and taking place through the cell membrane.

The essence of the invention is the recognition of the fact, that the biostimulating effect is attributable in the first place to the application of polarized light rather than to that of laser light, and the laser light has such an effect only because it represents a form of polarized light, too. Consequently, the normal, incoherent light can also trigger a biostimulating effect, provided it is linearly polarized.

According to the invention a method has been provided for the stimulation of biological processes related to cellular activity, particularly for promoting the healing of lesions on the body-surface, i.e. wounds, ulcers and various epithelial injuries, during which the pathological area is irradiated with a light of given intensity in which the improvement lies in that the irradiation is carried out by a linearly polarized light containing non-coherent components of wavelength exceeding 300 nm.

According to a preferable embodiment the intensity of the irradiating light is adjusted between 20 and 150 mW/cm$^2$.

It is advantageous for the healing process if the irradiation is carried out in intermittent periods and the energy density of the light during the treatment does not exceed 5 J/cm$^2$. With such an energy the re-arrangement process in the membrane can reach a saturation and the application of higher energies might not provide further benefits.

The light beam used for the treatment should comprise substantially parallel rays of continuous or quasi-continuous spectral distribution at least in the 400–700 nm wave-length range and the beam should fall substantially normal to the surface to be treated.

If the sectional area of the light bundle is less than the area of the pathological body-surface to be treated, it is expedient to perform irradiation by displacing the beam of light and the area under treatment in relation to each other in such a way, that the circumferential region of the area under treatment is irradiated first, then approach is made towards the centre region in a circular path. It is preferable if the beam has at least a 3 cm$^2$ sectional area and the treatment is performed at normal room temperature.

According to the invention an apparatus has also been provided for the stimulation of biological processes related to cellular activity, particularly for promoting the healing of lesions on the body surface i.e. wounds, ulcers and various epithelial injuries, comprising a light source in which the improvement lies in that the light source comprises a lamp emitting non-coherent light with spectral components exceeding 300 nm, a light deflecting system placed in the path of the light beams to project the light into a given direction of treatment, and a polarizer inserted in said path to produce polarized light beams approaching the surface to be treated. In the preferable embodiment an ultraviolet filter and in given cases an infrared filter is inserted into the path of the beams.

In a preferable embodiment a reflector surface is arranged behind the lamp to reflect forward the backwardly projected light beams. The reflector surface can be made of a cold mirror having preferably a spherical shape or the shape of a paraboloid of rotation. The light source can be a normal incandescent bulb or preferably a metal-halogen bulb.

The polarizer may comprise a sheet polarizer, a specular polarizer, a Nicol's prism or any other means capable of producing polarized light beams.

The apparatus according to the invention is preferably mounted in a tubular housing, the length of which is sufficient for the suppression of diverging direct light beams with divergence angles exceeding 15°.

A fan is mounted behind the reflector surface to provide sufficient cooling.

In a preferable embodiment the light deflecting system comprises lenses. The lens, when mounted in front of the reflector surface and provided with different coating materials on each side for filtering out the ultraviolet and infrared wave-length components can offer preferable features from the point of view of directing the light. In an other embodiment the reflector surface is of the shape of a paraboloid of rotation and the lamp is arranged in the focus thereof, and a pressed glass plate is arranged in front of the lamp fixed to the reflector surface and it comprises an annular spherical specular surface.

In a further embodiment the lamp and the reflector surface are arranged in an end portion of a tubular enclosure and a specular polarizer is placed in the opposite end region thereof. The plane of the specular polarizer is inclined in relation to the optical axis of the directed light beam propagating in the enclosure, wherein the angle of incidence of the beams on this plane is equal to Brewster's angle. There is arranged preferably another enclosure beside the first one, with holes defined in the adjacent side walls thereof to enable the passage of light beams reflected from the specular polarizer and there is another mirror in the second enclosure, placed in the path of the reflected light beams to direct these beams in parallel with the optical axis. It is preferable if the second enclosure of this embodiment is mounted closely beside and in parallel with the first one and the angle defined between the reflecting mirror and the specular polarizer is double the complementary of Brewster's angle.

In order to increase the efficiency of polarization it is preferable if the specular polarizer comprises a plurality of plano-parallel plates, made preferably of transparent glass.

The stimulating effect of the treatment with polarized light on the healing of wounds, as suggested by the present invention can be demonstrated effectively by describing the experiences obtained during such a treatment applied to chronic wounds which had been lingering for years.

In response to the treatment the chronic wounds started to heal, first they got purged, then secretion reduced and later completely ceased. Blood-vessel endings appeared on the bases of the wounds, then epithelization started on the edges. The process of healing was continuous. The bases of the wounds got filled up, then they healed in some cases after crustation.

On the basis of cytological examinations of smears taken from the wound secretion before and after each treatment, the effects of irradiation with polarized light can be summarized as follows.

The irradiation increased the proportion of healthy leukocytes which are ready for phagocytosis, to the necrotic ones.

Not only the number of phagocytic leukocytes but also the intensity of phagocytosis increased significantly. This increase in intensity manifested itself both in the highly increased number of bacteria phagolysed by the respective leukocytes and in the higher percentage of healthy and phagocytic leukocytes among all leukocytes.

After a few number of treatments the cells taking part in the immunological protection, namely the eosinophile cells, lymphocytes and monocytes appeared in the smears.

Both the quantity and quality of granuli in the cytoplasm of the cells changed considerably under the effect of the treatment which was demonstrated by the appearance of clearly visible large granuli.

The quantity of fibrin fibers originally not or hardly observable in the smear, multiplied under the effect of the treatment, and the initially thin fibrins with a tendency toward disintegration, increased both in length and thickness and they were often arranged in bundles.

In response to the treatment the composition of immunoproteins in the secretion has changed which could also prove the starting and activation of humoral protection. Irradiation with polarized light facilitated the quantitative growth of immunoproteins, of course to different degrees in case of different fractions. The highest average growth was observed in the immunoglobulin M, being about $+85\%$ compared to the pretreatment average value, whereas the lowest increase of about $+21\%$ appeared in the immunoglobulin A fraction.

The biological effects described hereinabove are closely related to the phase transition associated with the change of conformation of the polar heads in the cell membrane's lipid bilayer, i.e. to the effect of polarized light exerted on the lipid bilayer. This can be explained by the supposition that the antigen structures being present in the vicinity of immune cells can provide an immune response under the effect of polarized light by triggering a non-specific response in or increasing the sensitivity of the immune cells which, inter alia, can contribute to the healing of wounds.

If polarized light changes the membrane structure of the lymphocytes, then this intensifies the activity of the receptors of the lymphocytes on one hand, and on the other hand the change in the membrane structure can directly activate the cyclic adenosin monophosphate, which can trigger the energy-generating process of the cell. These two effects can generate a local immunological response.

In the course of the triggered immune response lymphokins are released that are capable of starting an immunological chain reaction. This chain reaction involves the triggering of the factor MIF (Migration Inhibiting Factor) inhibiting the migration of makrophags, the factor MCF (Monocyte Chemotactic Factor), the factor NCF (Neutrophile Chemotactic Factor) and the factor ECF (Eosinophile Chemotactic Factor) and these factors together attract the monocytes, neuotrophile granulocytes and eosinophile cells to the affected area.

Consequently, the aforementioned cells will migrate to that particular area.

On account of the changes in the membrane structure, the quantity of factor SRF (Skin Reaction Factor) that increases the permeability of blood-vessels will increase, thus it facilitates the circulation and in this way the transportation of the protective cells in the blood stream to the wounded area.

The above described events facilitate the cellular immune response (with T lymphocytes, killer cells) and the humoral immune response by means of T-helper cells.

The transport through the cell membrane will also be facilitated by the fact, that the initially irregular configuration of particles in the interstitium take a regular formation under the effect of electric field induced by polarized light. The process of re-arrangement in response to an electrical field is described e.g. in the paper of H. P. Schwan and L. D. Sher "Alternating Current Field-Induced Forces and Their Biological Implications" (J. Electrochem. Society, January 1969, pp 22c–25c).

On the basis of the above described effects it can be stated that the application of polarized light in accordance with the present invention exerts a stimulating effect in general on biological processes related to cellular activity by controlling the behaviour of the cell membrane.

The invention will now be described through exemplary embodiments thereof, in which reference will be made to the accompanying drawings.

BRIEF DESCRIPTION OF THE DRAWINGS

In the Drawings

FIGS. 8 to 16a, b and c (where applicable) show various photomicrographic pictures of smears taken from wound secretions, demonstrating the cytological status before and after treatment, respectively;

DESCRIPTION OF THE PREFERRED EMBODIMENTS

According to the present invention it has been discovered that the application of polarized light of sufficient intensity that falls in a predetermined wavelength range can produce a biostimulating effect. Though there are numerous known ways for the generation of polarized light, in the following description the specific conditions will be summarized and demonstrated by exemplary embodiments which should be taken into account when polarized light sources are being used to stimulate the healing of wounds.

Figure 1:
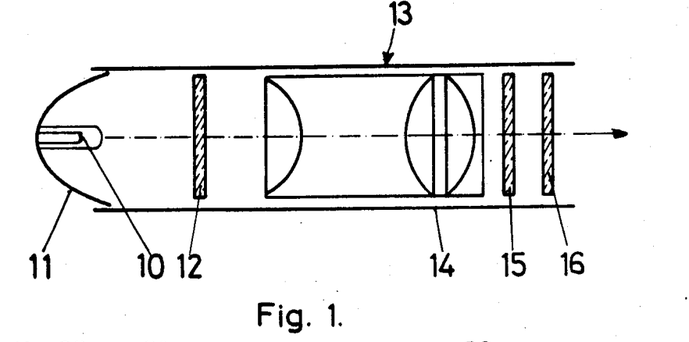
FIG. 1 is a simplified schematic sectional and elevational view of the first embodiment of the apparatus according to the invention.

FIG. 1 shows the schematic arrangement of a first embodiment of an apparatus for generating polarized light which can well be used for the healing treatment of wounds. The light source produced by lamp 10 is built integrally with reflecting surface 11 adapted to direct the backward light in an axially forward direction. If lamp 10 is a point source or nearly a point source and the reflector surface 11 has a rotational paraboloid shape, the majority of the light beams will be passed in parallel with the optical axis. In that case the lamp 10 should be placed in the focus of the reflector surface 11.

The next element in an axial direction after lamp 10 is infrared filter 12 for the suppression of infrared components emitted by lamp 10. The filtering or suppressing of the forwardly reflected infrared components will be more effective if the reflector surface 11 is designed as a cold mirror that fully reflects the visible components, whereas having a reflection factor in the infrared range being as small as about 20%, whereby about 80% of the backward infrared beams can pass therethrough. The infrared filter 12 can be of known type which is used commonly in photography such as the infrared filter type KG-4 of the Spezial-Glas GmbH (West Germany).

Figure 6:
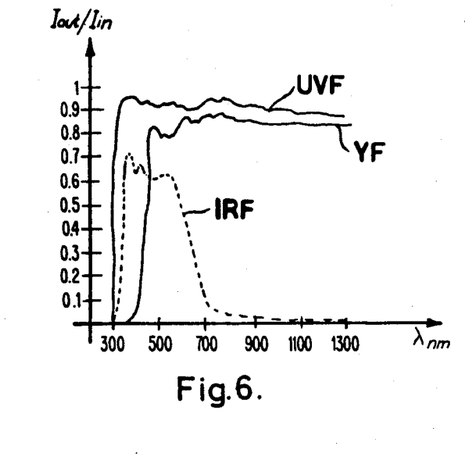
FIG. 6 is a graph which shows typical transmission characteristics of ultraviolet and infrared filters.

The transmission characteristics versus wavelength of a filter of this type is shown in FIG. 6 (curve IRF). The application of the infrared filter 12 is considered essential, because the heat load on the treated surface might cause undesirable effects (without the suppression of the infrared components). The density of the luminous flux of the predominantly visible light incident on the body-surface under treatment should be in the range of about 20–150 mW/cm.

In FIG. 1 a light deflecting system 13 is illustrated schematically. The task of the light deflecting system 13 is to project the light of the lamp 10 in parallel with the optical axis, by providing the most uniform spatial distribution possible. The deflecting system 13 can be built of traditional optical lenses, but the lamp 10 with the reflector surface 11 can also be regarded as an embodiment of the deflecting system 13, if they can produce together, the required axial light beams. The apparatus has a tubular enclosure 14 and by increasing its length the beams propagating non-parallel to the optical axis can be suppressed. Consequently it is not essential that the light deflecting system 13 be built of lenses. Indeed, the low value of the light intensity and the relatively significant light reflection is a disadvantage of the embodiments using lenses and due to the higher absorption more powerful bulbs should be chosen to provide a predetermined luminous output. On the other hand, however, the power of the lamp should be chosen as low as possible in order to minimize the problems of cooling.

It is well known in the art that the human body is sensitive to ultraviolet light. This sensitivity is even more intensive in case of ill tissues and wound surfaces, therefore the emitted light should not include ultraviolet components. The ultraviolet beams are effectively eliminated by filter 15. Though the ultraviolet range of the spectrum is filtered by the glass lenses, the application of a separate ultraviolet filter 15 is also advisable in combination with glass lenses. Thorough absorption of the ultraviolet range of the spectrum becomes particularly significant in embodiments operating without lenses.

In FIG. 6 curve UVF illustrates the transmission characteristic of an ultraviolet filter commonly used in photography. The absorption of the ultraviolet light will be more effective if the ultraviolet filter 15 is a yellow filter, also commonly used in photography. This results in a decrease in the visible light output mainly in the range of shorter wavelengths. Diagram YF in FIG. 6 shows the transmission characteristic of a typical yellow filter.

Linearly polarized light is produced by means of a sheet polarizer 16 placed in the path of the light beam. The sheet polarizer 16 can be made of a polarizing plate-filter commonly used in photography. Such a filter is e.g. the polarizing filter type 4K of the Spindler-Hoyer GmbH (W. Germany). Diagram PF in FIG. 7 demonstrates the transmission characteristic of such a filter. The dependence of polar absorption from the wave-length can be determined on the basis of the cross-over characteristics. To obtain such a characteristics a pair of polarizing filters of opposite polarization directions are placed behind each other and as a consequence of this arrangement the opposingly polarised light beams will mutually extinguish each other. Such a cross-over characteristic is shown in diagram CR of FIG. 7. It can be observed that in the infrared range, over the wavelength of about 800 nm, the phenomenon of extinction ceases, which indicates that such filters do not polarize the infrared part of the spectrum.

Figure 2:
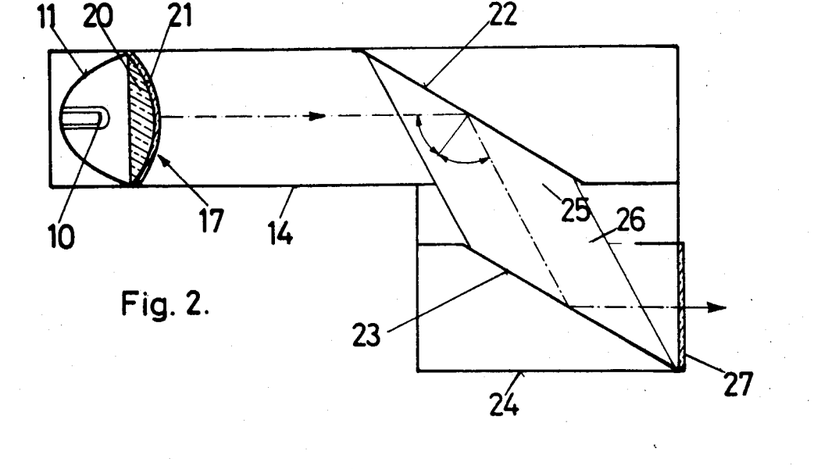
FIG. 2 is a schematic sectional and elevational view of a second embodiment.

FIG. 2 shows a further embodiment according to the invention. In this embodiment the lamp 10, the reflector surface 11 and lens 17 produce light beams parallel to the optical axis.

The lens 17 consists of two parts, namely of lens body 20 and of coating 21. The lens body 20 can be made by a glass material providing infrared absorption, in which case the coating 21 should be an ultraviolet filter. The function of the lens body 20 and the coating 21 can also be interchanged, in which case the former provides a UV-absorption and the coating is made of an infrared-absorbing material.

The light beams propagating in an axial direction in tubular enclosure 14 are transformed into polarized light by means of mirrors, as shown in FIG. 2. Specular polarizer 22 is mounted in the enclosure 14 in a remote position from the lamp 10 and in an inclined plane, in which the angle of incidence of the axial beams on this plane is 55°. Light is reflected from the specular polarizer 22 obliquely, in the direction shown with dashed-dotted line in the figure, and it strikes another mirror 23 arranged in parallel with the specular polarizer 22. The mirror 23 is mounted in housing 24, fixed to the enclosure 14. The reflected light beams pass through respective holes 25 and 26 made in the adjacent side walls of the enclosure 14 and of the housing 24. The mirror 23 reflects the light beams back into the axial direction. The housing 24 is closed by glass plate 27, which provides protection for the internal parts against dust and provides ultraviolet filtering. It is known from physics that mirrors arranged under a suitable angle relative to incident light can produce polarized light not only in the visible but also in the infrared ranges.

Figure 3:
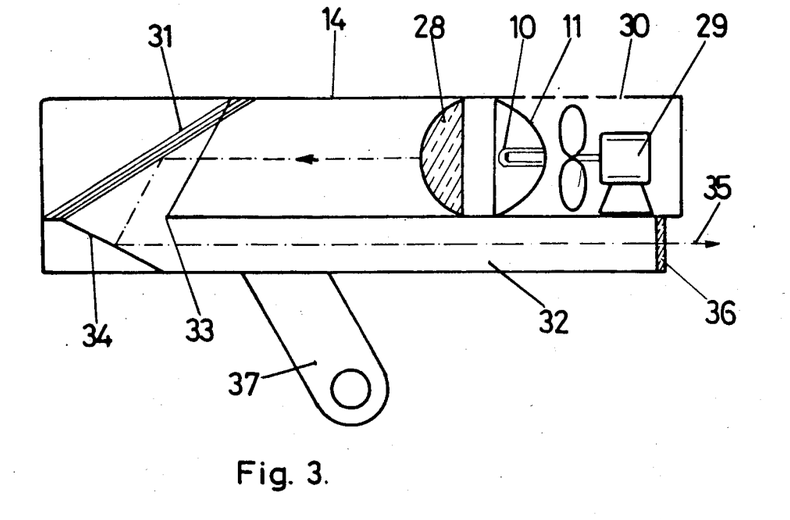
FIG. 3 is similar to FIG. 2, in which the direction of the light beams is reverse.

Reference is made now to FIG. 3, in which an embodiment similar to the one shown in FIG. 2 can be seen. The lamp 10 is built together with a spherical reflector surface 11 and in front of which a condensor 28 is placed. The reflector surface 11 is formed by a cold mirror, therefore a portion of the infrared beams are projected backwardly in a direction opposite to that of the visible beams, into a rear space behind the lamp 10. In this space fan 29 is arranged providing cooling both for the lamp 10 and the tubular enclosure 14. The cooling air streams out through vent holes 30.

The embodiment of FIG. 3 differs from that shown in FIG. 2 also in the arrangement of the light source in the right side of the enclosure 14 and in the opposing directions of the emitted and the outgoing light beams leaving the equipment. In this embodiment the polarizer is made by a plurality of plano-parallel plates of common transparent glass 31, being parallel to each other and being inclined relative to the direction of the incident light. The angle of incidence of the light is equal to the known Brewster's angle, which is 57°, and the light reflected from the layers consists of components which are polarized in one plane. The number of the reflecting surfaces of the plano-parallel layers 31 is double the number of the plates. About 35% of the incident light is reflected if the plate structure consists of four plates. Immediately under the enclosure 14 there is provided a second housing 32 of smaller dimensions built integrally therewith. The common wall of the enclosure 14 and the housing 32 defines a hole 33 having a size enabling the passage of all light beams reflected from each polarizer plate.

An inclined mirror 34 is placed in the path of the reflected light beams passed through hole 33 in such a way that the angle of incidence of the reflected light beams is also 57°. The mirror 34 reflects the incident light beams into a path which is parallel to the path of light emitted by the lamp 10 but having the opposite direction.

Figure 7:
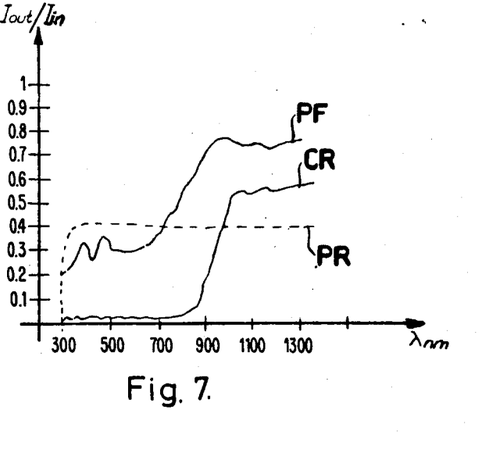
FIG. 7 is a graph which shows transmission and cross-over characteristics of different types of polar filters.

In this way reflected light beams 35 pass through the housing 32 and leave it at the right-hand end thereof. This end of the housing is closed by plate 36, made of an ultraviolet filter. The transmission characteristic of a polarizer of this type is shown in FIG. 7 (diagram PR). It can be seen that such polarizers provide polarized light also in the infrared region which eliminates the need of using an infrared filter. Owing to the wider polarized spectral range the required polarized light intensity can be reached with much less lamp-power relative to the designs with an infrared filter. The reduced power generates smaller amounts of heat, which renders the use of forced cooling unnecessary.

In the arrangement shown in FIG. 3 the path of the light is nearly twice as long as the total constructional length of the equipment, due to the reversing of the light beams. This increased length reduces the divergence of the outgoing light beams 35, because the divergent beams will be withheld by the tubular enclosure. It is advisable to provide the internal surface of the enclosure with a light-absorbing black coating. Another advantage lies in the fact that the sectional area of the enclosure 14 comprising the lamp 10 is larger than that of the housing 32, therefore a larger lamp can be used for a given outgoing beam cross-section which is preferable in view of heat engineering. Fan 29 is not essential, but it is recommended, particularly in the case of higher outputs.

During treatment it is often necessary to change the direction of the light beams. This function is performed by support 37 fixed to the enclosure 14 or 32, to be clamped to a console, not shown in the drawing. The console comprises known fixing and control mechanisms providing the required setting and position-adjustment of the light beams.

It should be noted that the embodiment shown in FIG. 3 is operative without the use of the second mirror 34 and the housing 32. In such an arrangement polarized beams are emitted in a downwardly inclined direction through the hole 33. The position of the enclosure 14 can be adjusted to provide polarized beams in any direction including both the horizontal and vertical ones.

Figure 4:
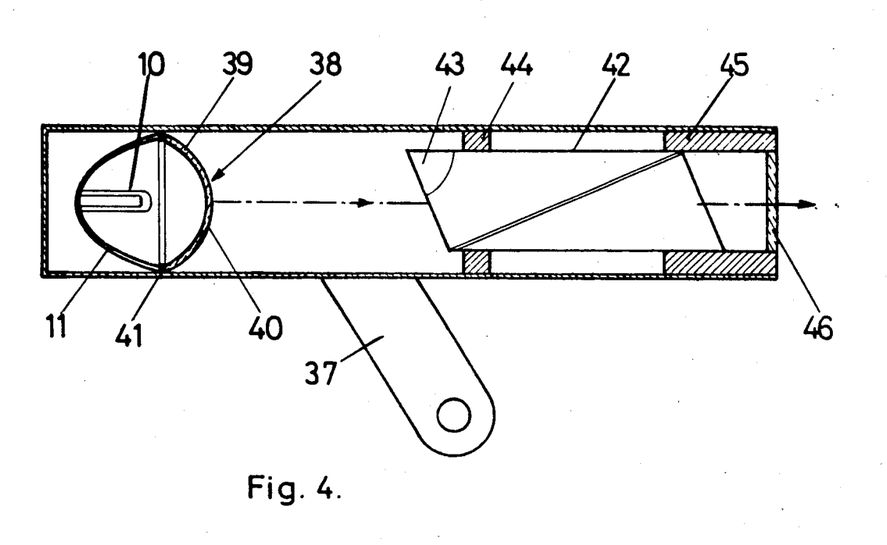
FIG. 4 is a similar view of a further embodiment, in which a Nicol-prism is used as polarizer.

A further embodiment of the apparatus according to the invention is shown in FIG. 4.

The light source used in this embodiment is of a special design capable of generating light beams substantially parallel to the axis. The lamp 10 is placed in the focus of the reflector surface 11 having now a shape of a rotational paraboloid. There is provided a pressed glass plate 38 fixed to the reflector surface 11 in front of the lamp 10. The pressed glass plate 38 has a spherical annular outer portion which is provided internally with a mirror surface 39 reflecting the incident light beams towards the centre of the lamp 10 which should now be regarded as a point light source. Within the internal annular edge of the mirror surface 39 the pressed glass plate 38 has a slightly convex form and this internal portion is made of transparent glass. The pressed glass plate 38 can be designed to form an infrared and/or ultraviolet filter.

Owing to this arrangement only light beams extending substantially parallel to the axis can pass through the transparent central portion 40 of the pressed glass plate 38. A ring 41 is provided to attach the pressed glass plate 38 to the reflector surface 11.

Whilst the mirror 39 is designed as a normal reflecting surface, it is recommended that the reflector surface 11 be made of a cold mirror.

It is believed that the compact lamp shown in FIG. 4 is the most appropriate for polarized light treatments which eliminates the need for using a separate light-deflecting optical system.

The polarizer shown in FIG. 4 is a per se known Nicol's prism consisting of a pair of calcite prisms tooled by grinding and glued together with Canadian balsam. Angle 43 shown in FIG. 4 is equal to 66°.

The Nicol's prism 42 is fixed in enclosure 14 by means of retaining washers 44 and 45. The retaining washer 45 has a frontal opening closed by glass plate 46, which can be designed as an infrared filter.

Figure 5:
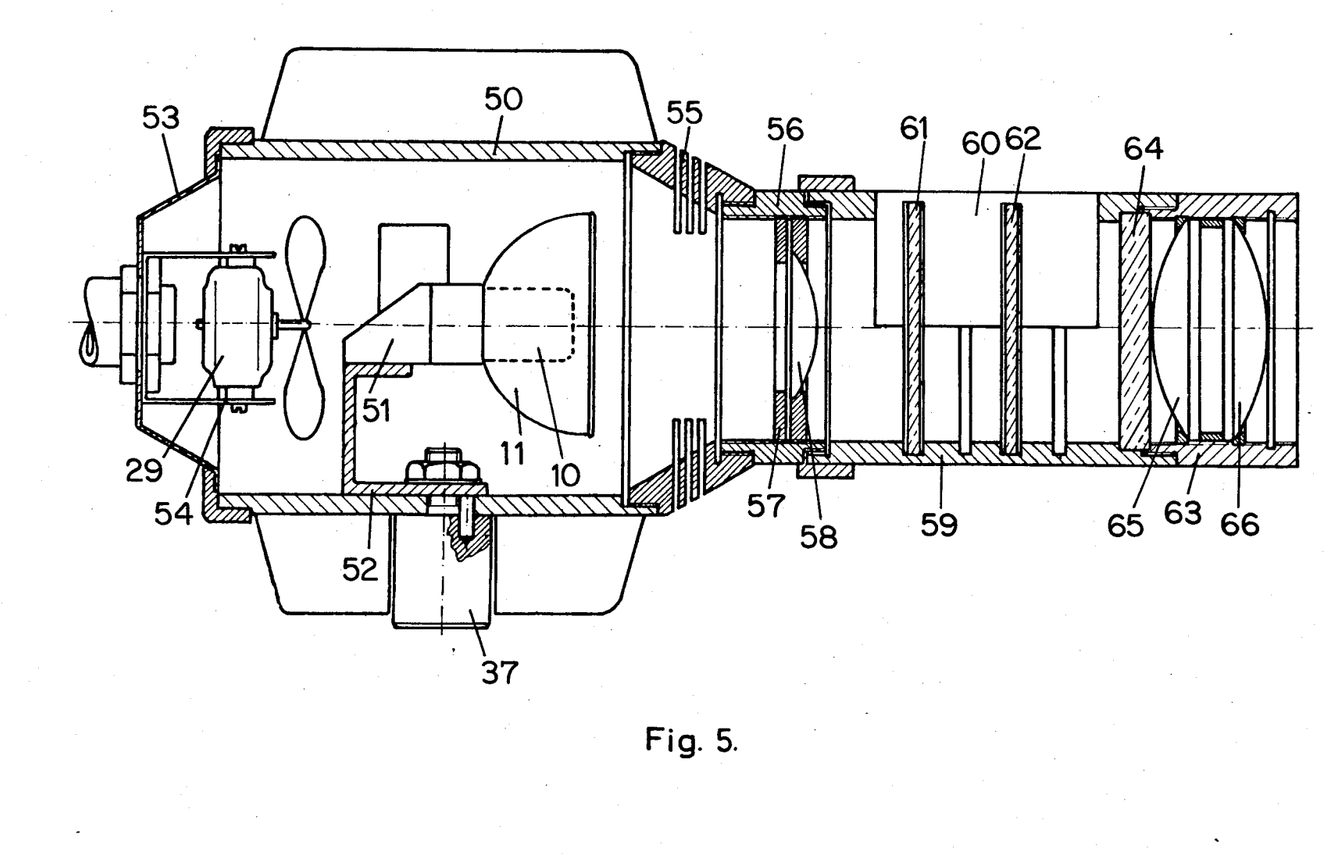
FIG. 5 is a detailed overall sectional and elevational view of the apparatus shown in FIG. 1.

FIG. 5 shows a more detailed assembly drawing of a polarized light source corresponding to the principal arrangement shown in FIG. 1. In this embodiment the lamp 10 and the reflector surface 11 are realized by the commercially available cold mirror-type lamp designated Tungsram 52210 or 52220 which is surrounded by a tube 50 provided with cooling ribs. The lamp 10 is fixed in a ceramic lamp socket 51, clamped onto a fixture 52 which together with a mounting base 37 is fixed to the lower part of the tube 50 by means of a screw joint. Disc 53 with vent-holes provides a rear closure for the tube 50. A hollow screw-mount is arranged in the centre of the disc 53 for supporting the electric cable connections and a bracket 54 adapted to fix the fan 29.

An adapter sleeve 55 with vent-holes is coupled to the frontal end of the tube 50 with cooling ribs and its frontal end is coupled to a sleeve 56 through a threaded joint. The sleeve 56 supports internally a lens holder 57 in which a lens 58 is mounted. The sleeve 56 is extended by a hollow filter support 59 designed to have an open top portion covered by a cover plate 60 attached thereto by a releasable fastening. There are several filter-holding slots (in the exemplary embodiment four slots) in the filter support 59. When the covering plate 60 is removed, suitable filters can be inserted into the respective slots of the filter support 59, or the filter can be changed according to actual requirements. In FIG. 5 infrared filter 61 and polarizing filter 62 have been shown in the slots of the tubular holder for filters. A tubular lens holder 63 is coupled to the filter support 59 in such a manner that an ultraviolet filter 64 can be inserted in the joint. The tubular lens holder 63 is used for holding second and third lenses, 65 and 66.

The apparatus shown in FIG. 5 produces polarized light beams of about 35–40 mm diameter, directed substantially in parallel to the optical axis. The emitted light falls within the visible range of wavelengths, and both its ultraviolet and infrared components are effectively suppressed.

On the basis of the embodiments shown in FIGS. 1 to 5 it can be stated that for the purpose of stimulating the healing of wounds a special light source is required that generates visible light, from which the ultraviolet (and as and if necessary the infrared) components are removed, the emitted light should propagate essentially in a parallel beam of uniform distribution. The light intensity of the beam should not exceed about 150 mW/cm$^2$. The emitted light should be linearly polarized.

The individual constructional details of the embodiments discussed hereinabove, can naturally be used in any other rational combination. For example, the light source demonstrated in FIG. 4 can be employed in the arrangement according to FIG. 1, however, that would render the use of deflecting system 13 unnecessary. Thus, the polarized light source according to the invention should not be limited to any one of the exemplary embodiments.

Now the application of the method according to the invention and the experiences obtained during such applications will be described through the following examples.

In order to demonstrate the effect of polarized light, patients were treated with anamnesis in which all types of traditional therapy for healing their wounds had been applied, without even a temporary success. Altogether 23 patients were treated and the aetiological distribution of their illness was the following: ulcus cruris developed as a consequence of diabetic angiopathy in the case of 7 patients; ulcus cruris was caused by arteriosclerosis obliterans in 6 cases, and in 6 cases by varicositas or postthrombotic syndrom. Three patients were treated for decubitus and one of the patients had a chronic osteomyelitis in the background of his pathography.

Prior to the treatment with polarized light, during the traditional therapy, dressings with Mikulitz's ointment and Peruvian balm, Oxycort, Panthenol spray, Solcoseryl jelly, Debrisan and various local antibiotic and drying bandages were employed. As a general therapy, the patients took Glyvenol, Padutin, Venoruton, vitamins and other corroborants, and they also received corroborant treatment. The treatment with polarized light was started after the failure of the above mentioned types of conventional therapy. Mentioning only the extreme cases, one of the patients had a non-healing wound for more than 35 years, and in several cases the wounds developed 5-20 years before the treatment was started.

The treatment with polarized light was performed once a day. The area of the spot of the light projected onto the wounds was about 4 cm$^2$ and the average flux-density of the beams was about 80 mW/cm$^2$. The spectrum of the light ranged between 300 nm and 700 nm, the spectral distribution did not comprise discrete components with high intensities.

The duration of the treatment was chosen so that the average energy falling on the wound surface under treatment be 4 J/cm$^2$. When the area to be treated was larger than the cross-section of the beams, this latter was scanned by the intermittent displacement of the light source in such a way that the wound edges were irradiated first circumferentially and the inner region was reached by a circular inwardly directed movement. The typical duration of the treatment in each position of the light source was between one and two minutes.

Before and after each treatment respective samples were taken from the wound secretion and smears were prepared for microscopic evaluation using fixation technique and the May-Grünwald-Giemsa method. With the progress of the treatment as the secretion was gradually reduced and ceased, smears could not be prepared any more.

In addition to the samples for smears larger samples were also taken from the wound secretion—when it was possible—to determine the composition of proteins, particularly immunoproteins, in the serum.

For the duration of the treatment with polarized light the patients did not get any kind of antibiotics and only dry bandages were applied.

On the basis of the cytological examination of smears, taken from the wounds before and after every treatment, the following general results have been obtained:
(a) The ratio of healthy leukocytes ready for bacterio-phagocytosis to the necrotic ones increased to a substantial degree as a consequence of irradiation with polarized light. The increase of this ratio showed a fairly varied picture in the examined cases. It occured in several cases that, whilst there were no healthy leukocytes at all in the smear before treatment, the ratio of healthy leukocytes to the necrotic ones increased to 50%:50% in the smear prepared immediately after treatment.

Irradiation with polarized light facilitated the emergence of healthy leukocytes on the wound's surface. The extent of increase of this ratio in favour of the healthy leukocytes could be observed nearly in each sample, however, it was particularly high after the first few treatments of a series.

Most of the leukocytes in the smear were neutrophil granulocytes forming the basis of the cellular defense mechanism of the organism, which is the most elementary form of protection. Sacrificing themselves, the neutrophile granulocytes swallow bacteria in order to protect the organism. The measure of the intensity of bacterio-phagocytosis is the number of bacteria swallowed by a single neutrophile granulocyte.

FIGS. 8a, 8b, 9a and 9b demonstrate these phenomena.

Figure 8A:
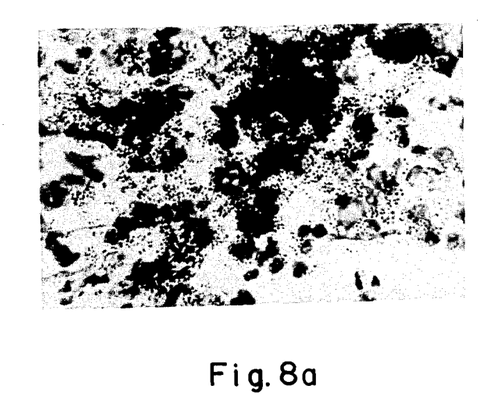
Figure 8B:
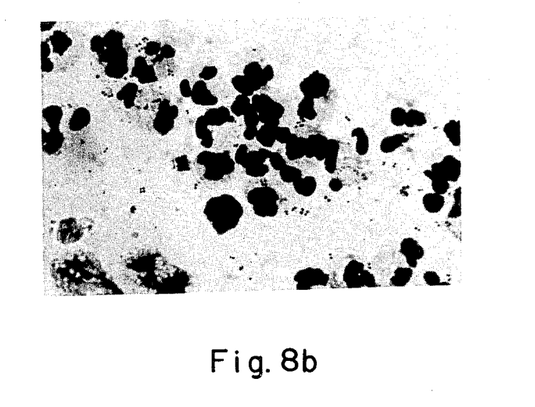

FIG. 8a shows a smear taken before treatment in which a great number of extracellular bacteria can be observed and the overwhelming majority of the leukocytes is formed by necrotic ones. The situation after treatment is illustrated in FIG. 8b, extracellular bacteria have substantially vanished and mainly healthy leukocytes can be seen.

Figure 9A:
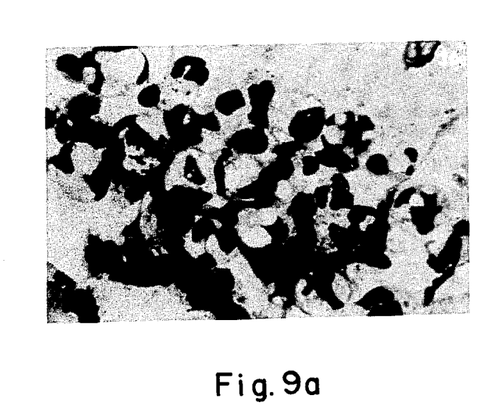
Figure 9B:
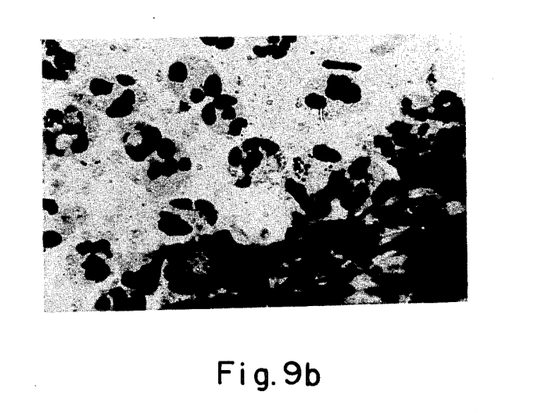

Another typical smear is shown in FIG. 9a, in which the number of necrotic cells was high before treatment, and after treatment as shown in FIG. 9b, a substantial increase occured in the number of healthy cells.
(b) The intensity of phagocytosis has also increased. In addition to the increase in the ratio of healthy phagolytic leukocytes, the intensity of phagocytosis has also increased as a consequence of irradiation with polarized light. The rather sluggish bacterio-phagocytosis before treatment, which meant the swallowing of about 8-10 bacteria by a single cell, was becoming more and more intensive, and the leukocytes phagolysed up to 80-100 bacteria under the effect of treatment.

The intensity of phagocytosis is also characterized by the percentual ratio of the actually phagolysing leukocytes within total number of healthy ones. Whilst only 5-10% of the healthy leukocytes were phagocytic before treatment, after treatment this ratio increased to 50-60%.

These two phenomena are particularly significant in the initial phase of healing, because the healing of wounds is impeded mainly by the presence of extracellular bacteria.

The appearance of sound healthy leukocytes in the secretion and both types of the intensification of bacterio-phagocytosis promote the annihilation of extracellular bacteria.

Figure 10A:
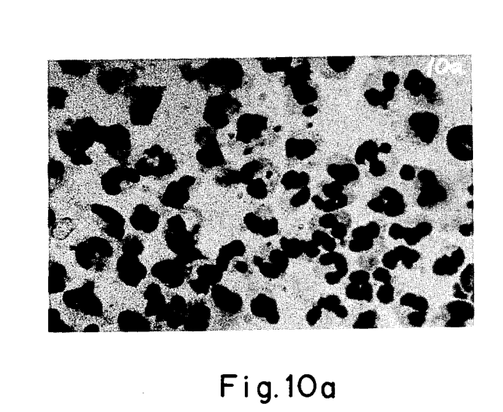
Figure 10B:
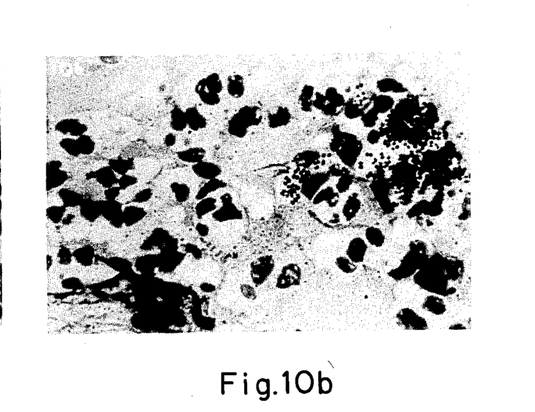
Figure 11A:
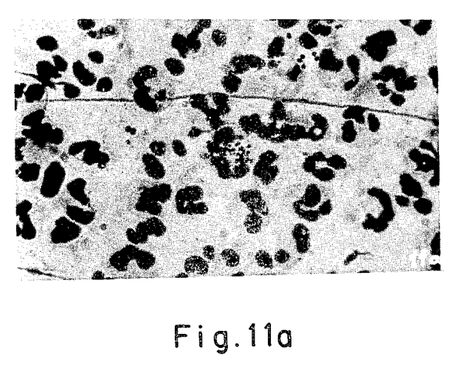
Figure 11B:
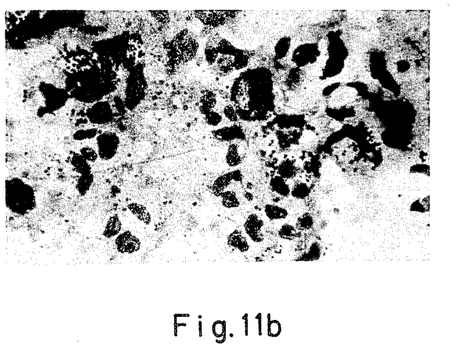

FIG. 10a shows a situation before treatment, where only few cells phagolyse and each of them swallows only few bacteria. FIG. 10b shows the situation after treatment and it demonstrates that the number of phagocytic cells and the number of bacteria swallowed by one cell has increased noticably. A similarly considerable intensification can be seen in FIGS. 11a and 11b, illustrating also respective situations before and after irradiation. The smears taken after irradiation also demonstrate the disappearance of extracellular bacteria.
(c) Under the effect of the treatment with polarized light the immunological (humoral) defense of the organism is also triggered or intensified.

It is known that this type of protection against bacteria is provided by plasma cells, lymphocytes and monocytes. These types of leukocytes produce immunoproteins, killing the bacteria. The appearance of these cells means that the organism mobilizes deeper immunological mechanisms to heal the wound and kill the bacteria.

While the smear taken before irradiation contained generally neutrophile granulocytes only, after irradiation other types of leukocytes have also appeared that can provide higher, humoral form of protection. Such cells are e.g. the eosinophile cells, lymphocytes and monocytes.

In several cases these cells appeared already after a few treatments. The ratio of appearance of these cells relative to other cells varied from one case to the other. It happened that no lymphocytes were found among the leukocytes before treatment, whereas the ratio of lymphocytes increased to 4-10% by the end of the treatment. With increasing number of treatments lymphocytes could be seen in the secretion already before the next day's treatment, but their ratio before treatment was, for example, 2%, which increased to 20% following the treatment.

A similar phenomenon was observed in the case of eosinophile granulocytes, the ratio of which increased from the initial 0% to 1-5%, then in a later phase of the therapy from the initial 1% to 20%. Similar increase of the percentual ratio of monocytes was detected from the initial 0% to the post treatment 5% and in a later phase from 3% to 5%.

The cells that provide the immunological defense of the organism, appeared generally after the second or third treatment, but a significant quantitative growth could be observed generally during and after the seventh-ninth treatment. However, the presence of these cells stabilized only after the 15th-20th treatment, up to which their quantity decreased between subsequent treatments.

By that time there were already visible signs of the ongoing healing process. This is a rather significant demonstration, since before the first treatment there were no traces of the presence of leukocytes in the secretion of any of the patients that would provide immunological defense.

Figure 12A:
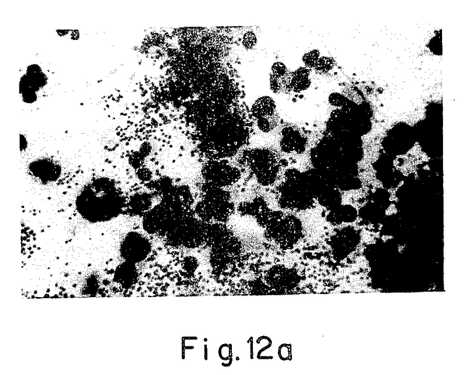
Figure 12B:
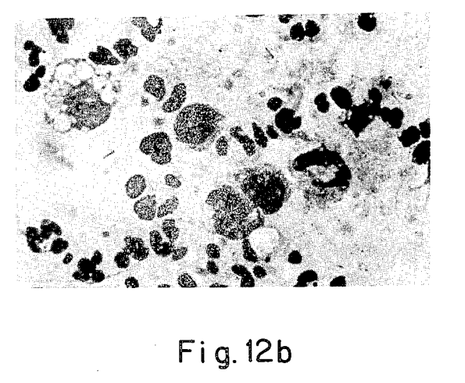
Figure 12C:
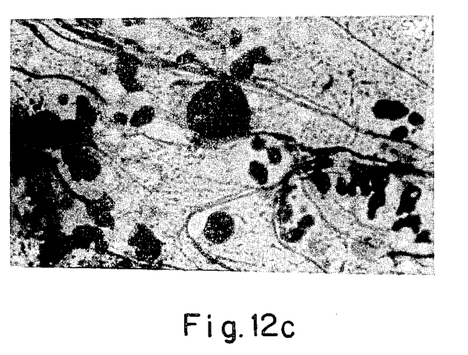
Figure 13A:
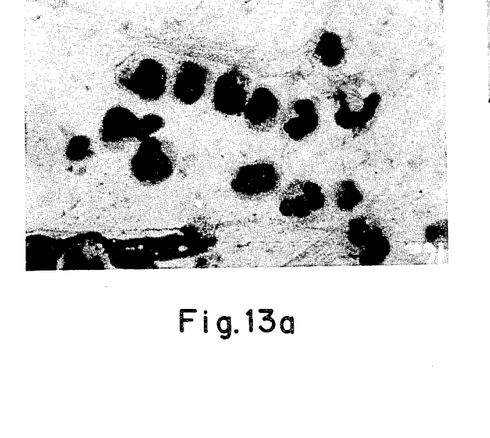
Figure 13B:
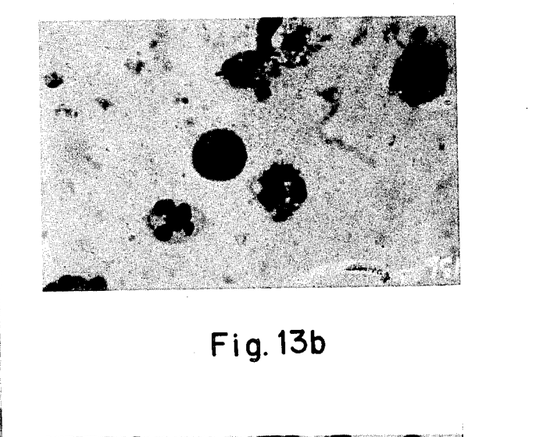
Figure 13C:
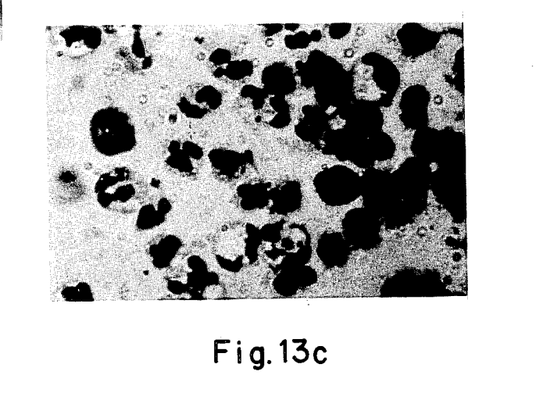
Figure 14A:
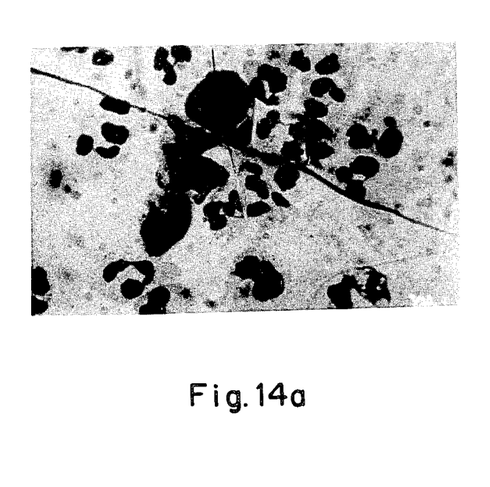
Figure 14B:
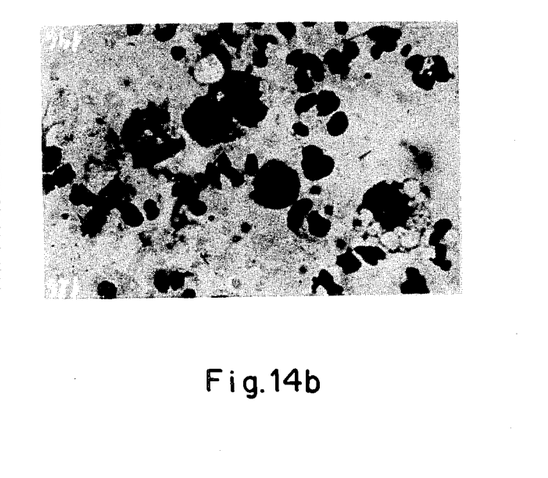

FIG. 12a shows a condition before treatment with visibly high number of extracellular bacteria and sluggish bacteriophagocytosis. Apart from the neutrophile granulocytes no other types of leukocytes can be seen. FIG. 12b shows the situation after treatment and it can be seen that some lymphocytes have appeared, and the extracellular bacteria have disappeared. After a later treatment monocytes can be detected (see FIG. 12c). In FIG. 12c it can also be observed that fibrin-fibers are already present. Similarly, FIG. 13a illustrates a pretreatment condition with low granularity. Only neutrophile granulocytes can be seen. After treatment the eosinophile cell has also appeared (see FIG. 13b). After successive treatments a great number of eosinophile cells appear in the smear as shown in FIG. 13c. In FIG. 14a lymphocytes can be detected even before the treatment and the quantity of which has considerably increased after the treatment (FIG. 14b).

When the process of healing is examined, it will be discovered that at first the quantity and activity of the neutrophile granulocytes increases in a chronic, refractory wound and after that, or partly at the same time cells offering the higher forms of protection appear, and when these mechanisms of protection become relatively stabilized, the spectacular process of healing of the wound starts.

(d) The evolution of immunological protection is verified by the change in the quality and quantity of granuli in the cytoplasm of the cells, taking place under the effect of the treatment.

Granulation comprises the lysosomatic enzymes (that can dissolve all types of organic matter required for protection against bacterii) and the presence of a definite, large-size granulation is the proof of the quantitative growth and appearance of such enzymes.

Figure 15A:
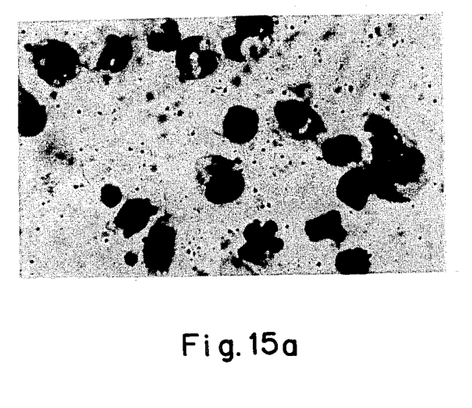
Figure 15B:
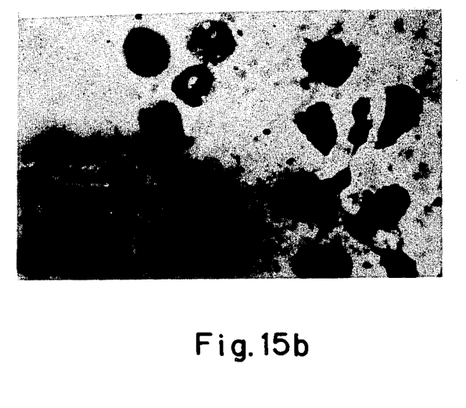

FIGS. 15a and 15b demonstrate the changes in extent and quality of granulation that occured in response to the treatment with polarized light. Before the treatment the granulation in the neutrophile granulocyte cells was weak, hardly detectable. In the post-treatment state as shown in FIG. 15b a definite, large-grained and well detectable granulation can be seen in the cytoplasm of the cells.

(e) The few fibrins when being present in the pre-treatment smear are thin with a tendency toward disintegration.

Figure 16A:
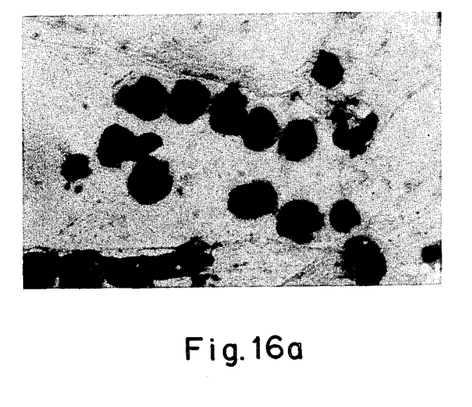
Figure 16B:
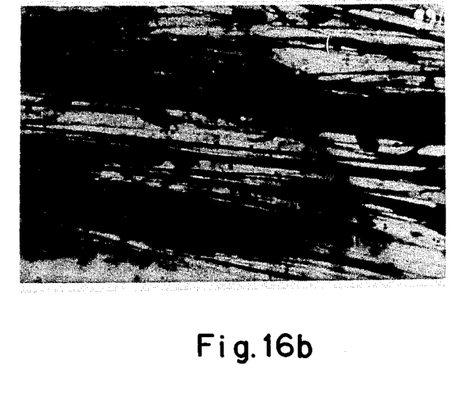

The presence of fibrins in the course of the first few treatments was hardly experienced. In response to the treatment with polarized light the quantity of fibrins multiplied in relation to the pre-treatment condition. These fibrins are formed to long, thick, parallel straight fibres arranged often in bundles. This is illustrated in FIGS. 16a and 16b showing smears taken before and after irradiation, respectively. The effect of treatment with polarized light on the composition of immunoproteins in the secretion has also been investigated. The composition measurements were carried out by the immunoelectrophoretic technique. 0.4 μl volume of the secretion was required for each analysis to prepare the samples on a specially prepared plate for immunological tests. Eight different proteins can be measured usually on a single plate. There is a standard sample on each plate, in which the respective areas pertaining to each fraction are known, therefore the measurement can be performed to supply not only relative, but also absolute values.

Figure 17A:
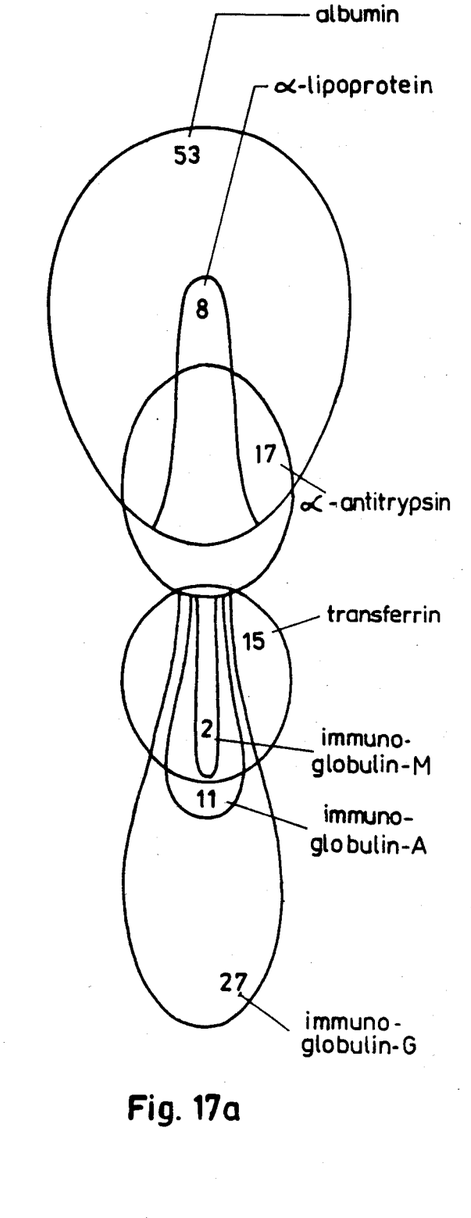
FIGS. 17a and b show patterns used for the measurement of immunoprotein fractions in samples, taken before and after treatment, respectively.
Figure 17B:
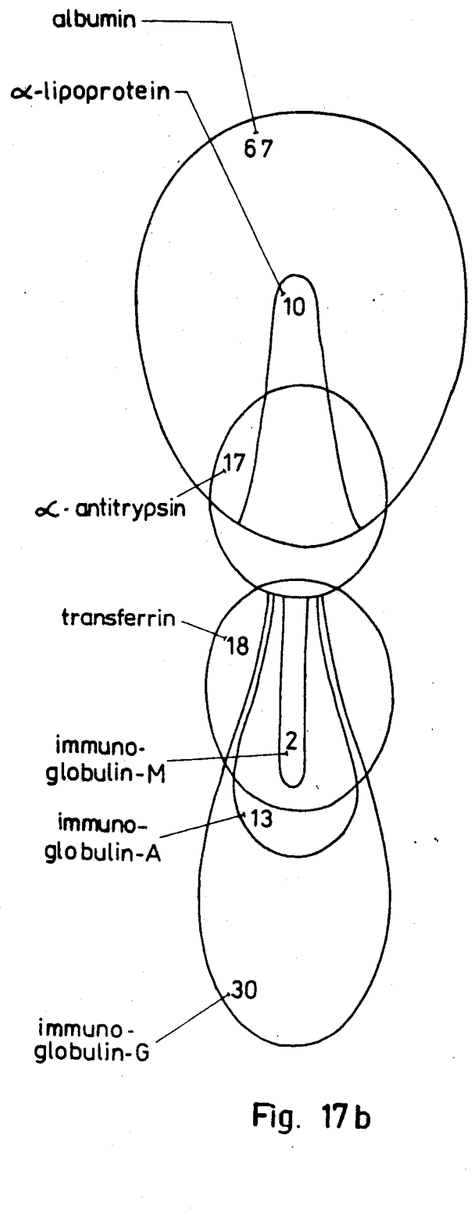

During immunoelectrophoresis the individual protein fractions separate, and the quantitative ratios of fractions are represented by the ratios of the corresponding areas. By placing the test plate onto an overhead projector and outlining the contours of each fraction projected with the same magnification, the size of the obtained areas can be determined by means of a planimeter. Then the quantities of the fractions are calculated in relation to the standard areas. Such outlined contours are shown in FIGS. 17a and 17b (before and after treatment, respectively). The figures associated with the respective components indicate the relative indices of the related areas.

In the course of the measurements the composition of immunoproteins in the secretion of three patients was analysed and the samples were taken before and after each treatment of a series. The effect of the treatment is reflected in the extent of change of the composition. Table 1. shows the percentual changes of immunoprotein fractions of three patients A, B and C, in response to respective treatments. The missing entries indicate that the low quantity of the secretion that was available during the particular treatment, was not sufficient to perform the measurement of that particular component. In case of patient C, due to the rapid healing of the wound, sufficient amount of secretion was available during a few treatments only.

TABLE 1

Percentual changes of the respective components after treatment relative to pre-treatment values

| Sample number | Albumin | | | Immunoglobulin G | | | Immunoglobulin A | | | Immunoglobulin M | | |
|---|---|---|---|---|---|---|---|---|---|---|---|---|
| | A | B | C | A | B | C | A | B | C | A | B | C |
| 1 | 125 | 126 | 239 | 73 | 111 | 150 | 74 | 118 | | 100 | 100 | |
| 2 | 80 | 126 | 600 | 135 | 107 | 433 | 146 | 100 | | 200 | 100 | |
| 3 | 140 | 114 | 57 | 118 | 117 | 61 | 118 | 127 | 67 | 200 | 100 | 50 |
| 4 | 120 | 377 | 175 | 112 | 236 | 239 | 120 | | 192 | 100 | | 350 |

TABLE 1-continued

Percentual changes of the respective components after treatment relative to pre-treatment values

|   |     |     |     |     |     |     |     |     |
|---|-----|-----|-----|-----|-----|-----|-----|-----|
| 5 | 132 | 110 | 121 | 115 | 131 | 112 | 50  | 149 |
| 6 | 81  | 97  | 91  | 100 | 94  | 100 | 100 | 200 |
| 7 | 96  | 84  | 92  | 100 | 87  | 116 | 100 | 100 |
| 8 | 104 |     | 103 |     | 111 |     | 167 |     |
| 9 | 120 |     | 123 |     | 109 |     | 200 |     |
| 10| 132 |     | 142 |     | 149 |     | 200 |     |
| 11| 94  |     | 96  |     | 92  |     | 100 |     |
| 12| 137 |     | 133 |     | 133 |     | 200 |     |
| 13| 125 |     | 205 |     | 150 |     | 223 |     |
| 14| 123 |     | 104 |     | 91  |     | 100 |     |

| Sample number | $\alpha_1$-Lipoprotein | | | Transferrin | | | $\alpha_2$-Macroglobulin | | | $\alpha_1$-Antitrypsin | | |
|---|---|---|---|---|---|---|---|---|---|---|---|---|
|   | A | B | C | A | B | C | A | B | C | A | B | C |
| 1 | 100 | 125 | 275 | 70  | 120 | 90  | 70  |   |   | 76  | 100 |     |
| 2 | 122 | 100 |     | 142 | 100 |     | 142 |   |   | 132 | 100 |     |
| 3 | 180 | 107 | 53  | 124 | 120 | 54  |     |   |   | 118 | 121 | 57  |
| 4 | 120 | 400 | 330 | 127 | 299 | 284 |     |   |   | 123 |     | 300 |
| 5 | 150 | 108 |     | 141 | 107 |     |     |   |   | 131 | 108 |     |
| 6 | 70  | 100 |     | 92  | 88  |     | 100 |   |   | 100 | 77  |     |
| 7 | 131 | 90  |     | 92  | 111 |     | 111 |   |   | 94  | 100 |     |
| 8 | 109 |     |     | 109 |     |     | 118 |   |   | 100 |     |     |
| 9 | 56  |     |     | 124 |     |     | 167 |   |   | 120 |     |     |
| 10| 136 |     |     | 165 |     |     | 140 |   |   | 171 |     |     |
| 11| 90  |     |     | 76  |     |     | 80  |   |   | 83  |     |     |
| 12| 143 |     |     | 150 |     |     | 179 |   |   | 137 |     |     |
| 13| 324 |     |     | 233 |     |     | 200 |   |   | 270 |     |     |
| 14| 100 |     |     | 111 |     |     | 80  |   |   | 124 |     |     |

On the basis of Table 1, in which the respective pre-treatment values have been considered as 100%, it can be seen that irradiation with polarized light intensifies proteinogenesis in the secretion, obviously to different degrees in different fractions. The considerable fluctuations in the entries of the table resulted by the individual differences and by the fact that the samples were taken in different phases of healing. There was no sense of calculating averages due to the high variance of the values, however, the data of table 1 clearly demonstrate the tendency of quantitative growth of the components in response to the treatment. These figures show that the highest increase took place in fraction immunoglobulin-M, then the succession was: Albumin, $\alpha_1$-lipoprotein, Immunoglobulin-G, $\alpha_1$-antitrypsin, Transferin, $\alpha_2$-Macroglobulin and Immunoglobulin-A.

It has also been noticed that the inclination to healing of different patients is proportional to the quantitative growth of immunoproteins that take place in response to respective treatments. The more is the increment of immunoproteins, that is, the more intensive is the response to the treatment with polarized light, the higher is the rate of healing. Taking this relationship into account, the inclination of the wound to healing and the expected total duration of the cure can be estimated already on the basis of a few treatments.

The results of the immunological tests are in accordance with the experiences obtained by the cytological examinations, i.e. in response to the treatment with polarized light:
  (i.) protein types providing humoral protection appear,
  (ii.) definite granulation, indicating the presence of lysosomatic enzymes, appears in the cytoplasm of the cells;
  (iii.) effective protection starts against the bacilliform bacteria, destroyable mainly in the immunological way. Besides cytological and immunological tests, great importance was attached to the general process of healing as well.

In the course of the examinations the macroscopic parameters of the wounds were measured and the obtained results were evaluated. The changes observed in the base of the wounds were measured and recorded including the vertical and horizontal dimensions of the edges of the wounds, as well as their depths and the width of the newly grown epithelial edges were also measured. In the course of treatments the wounds began first to purge, secretion reduced and became clearer even after a few treatments only. At the same time the patients reported on the substantial reduction of their pains. The wounds started to heal visibly after a certain period of latency, which lasted generally one week. After this time the wounds started to heal gradually, even those which showed no tendency of healing before the treatment with polarized light.

After another week of treatment the process of healing usually became more rapid.

Blood vessel endings appeared on the bases of the wounds later with white pearly growths around them, and epithelisation also started on the edges. The new epidermis appeared first as a red area that usually turned white and became a rim-like elevation to the next day.

The beginning and rate of healing largely depends on the age, general condition, medical and haemodynamic state of the patient.

Figure 18:
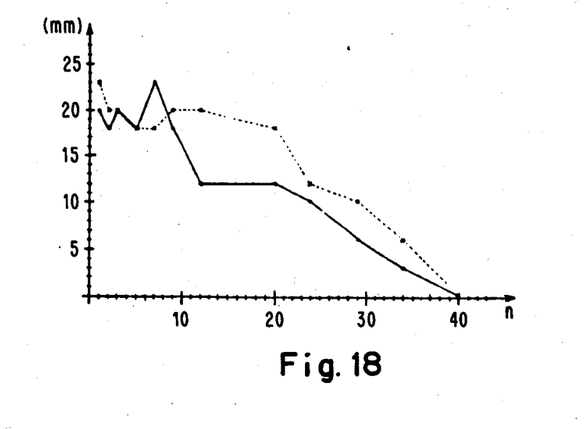
FIGS. 18 to 20 are various diagrams illustrating the vertical and horizontal sizes of wounds during the process of healing.
Figure 19:
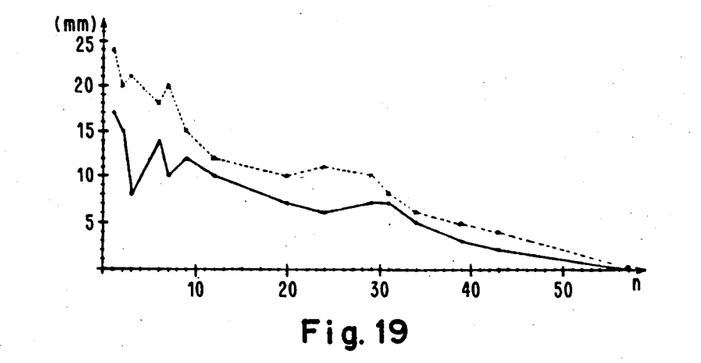
Figure 20:
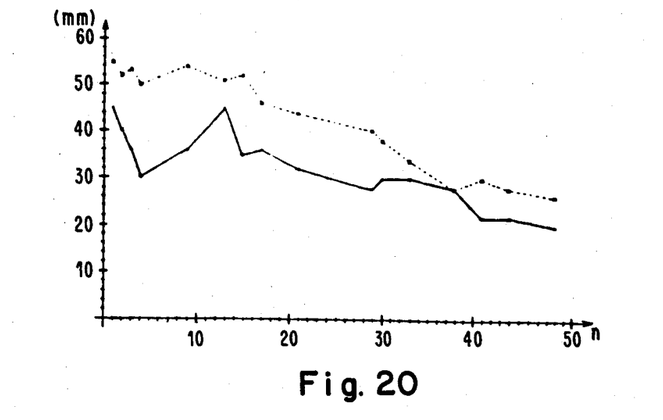

This process is illustrated by FIGS. 18, 19 and 20. The full lines show the horizontal size of the wounds and the dash lines the vertical one.

In the anamnesis of a 54 years old male patient the only disease he suffered from was hepatitis. He has had distinct varicosity for 20 years, but he hasn't had thrombosis. His shin split a first time 15 years ago, then the wound healed spontaneously. This process was repeated since then several times. The ulcer developed on his right shin four years before; the current wounds have not healed since 10 months. He was treated with Venoruton and Padutin, the local medical attendance involved Oxycort, antibiotics, Neogranorman and Panthenol.

The treatment with polarized light was started after such antecedents. At that time he had a 2 mm deep ulcer of 20×24 mm size on the border of the middle and lower third of his shank, and a 4 mm deep one of 24×18 mm size in the distal third. Approximately after the 5th or 7th treatment the wounds started to heal rapidly, they became shallower and nervate. The distal wound healed with crustation to the 40th treatment (FIG. 18), then the much deeper proximal ulcer also pullulated to the 57th treatment (FIG. 19), and the cure was finished.

FIG. 20 demonstrates the healing of the wounds of a 66 years old male patient. His anamnesis included permanent coxalgia for 21 years, therefore he was provided with an artificial hip (prothesis) 17 years ago and in order to relieve him of lingering pain, cordothomy was performed on him. Due to his mental derangement, which evolved six months before, he was transferred to the psychiatric department. On the body of this patient, who became confined to bed in the meantime, decubiti evolved gradually, on both sides, on the hip and sacralis too. Then the treatment with polarized light was started. At the beginning of the therapy he had two 3 mm-deep wounds on the rightside of the hip, one of 21×30 mm and the other of 16×25 mm size. On the left side he had a 38 mm deep wound of 66×45 mm size. The sacral decubitus was 30×13 mm large. The effect of the polarized light began to purge the wounds gradually and after the 7th treatment their size started to recede slowly. Then the rate of healing decelerated temporarily and after the 40th treatment the pouches on the edges subsided and the depth of the hollow also decreased considerably. The patient left the ward upon his request, due to some family affair, after the 50th treatment. At this time the sacral ulcer and the smaller wound on his right side were entirely epithelised, the other one receded to 8×17 mm, and the wound on his left side—to 26×20 mm.

The experiences obtained by polarized light treatment show that lesions due to diabethes react to the treatment after the longest time and with the slowest rate. The inclination to healing of wounds, developed as a consequence of arteriosclerosis obliterans is somewhat better, but the most striking and rapid are the results obtained in the curing of ulcus cruris developed due to postthrombotic syndrom.

In the foregoing description the stimulating effects of the treatment with polarized light have been demonstrated on the healing of chronic, otherwise non-healing wounds. It became clear that the treatment exerted a significant stimulating effect on the healing process even in case of the most unfavourable pathography. It must be obvious therefore that the stimulating effect of the treatment with polarized light also asserts itself in the healing of acute injuries, cut and contured wounds, where the conditions hindering the healing process are less manifested.

According to the experiments, treatment with polarized light also facilitates the healing of burning lesions. On the leg of a 40 years old male patient autograft was performed for the treatment of a third-degree burn. The skin-graft separated on an area of 1×5 cm size, and two additional areas of 1 cm² each. The physicians performing traditional treatment suggested a new transplantation, because by their opinion the process of pullulation from the edges of the wound would take several months.

After these antecedents started the treatment of the wound surface with polarized light, once a day, at 4 J/cm² density of energy. Following the third treatment pullulation started from the edges of the wound. Then the process of healing sped up, in two weeks full crustation took place, then, having finished the treatment, the whole surface healed. The treatment with polarized light was applied in those places only, where the skin-graft separated.

Whilst the transplanted skin surface, not treated with polarized light was of reddish hue with secondary pouches, the colour of the recovered skin irradiated with polarized light was natural, its surface was smooth, and this was the strongest, soundest portion of the healed area of the third-degree burn.

Considering that the treatment with laser light has been applied in numerous fields of clinical practice during the long years elapsed since its introduction, and the biostimulating effect has been proven, it may be supposed that the biostimulating effect can also be triggered in similar fields of application through treatment with polarized light.

This may apply to various treatments of cosmetic nature, to the liquidation of cicatrices, to the stimulation of miscellaneous lesions on the body-surface on the analogy of laser stimulation, or, in general, to stimulate biological processes, related basically to cellular activity.

We claim:

1. Method for in vivo stimulation of biological processes relating to cellular activity in a region of cells, comprising the step of irradiating the in vivo region to be stimulated with light of predetermined intensity, said light being linearly polarized and non-coherent and predominantly including wavelength components exceeding 300 nm and substantially excluding ultraviolet components and non-polarized infrared components.

2. Method of claim 1, wherein said intensity is between 20 and 150 mW/cm².

3. Method of claim 2, wherein said step of irradiation is carried out in intermittent periods and the energy applied during each period is at most 5 J/cm².

4. Method of claim 1, wherein said irradiating light has one of a continuous and quasi-continuous spectral distribution at least in the 400–700 nm range of wavelengths.

5. Method of claim 1, wherein said light comprises substantially parallel beams forming a bundle.

6. Method of claim 1, wherein said region is irradiated from a direction substantially normal thereto.

7. Method of claim 1, wherein said light is a light bundle having at least 3 cm² sectional area.

8. Method of claim 1, wherein said step of irradiation is carried out in an environment at normal room temperature.

9. Method of claim 1, wherein with a sectional area of said irradiating light which is less than that of said region to be irradiated, said light and said region are displaced with respect to each other, said light radiating circumferential areas of said region first and then approaching a center area of said region along a circular concentric path on said region.

10. Method of claim 1, wherein said light is filtered from ultraviolet components and from non-polarized infrared components.

11. Method of claim 1, wherein said light is filtered from ultraviolet components and comprises infrared components which are subjected to linear polarization.

12. Device for stimulating biological processes in an area, comprising:

a housing defining a space for containing a light path, a light source for generating non-coherent light predominantly including wavelength components exceeding 300 nm and containing infrared components of wavelength in said housing, deflecting means arranged for directing the non-coherent light into a beam on said path, a polarizer arranged for polarizing the non-coherent light beam on said path including infrared components of said light beam, and filter means arranged for filtering out ultraviolet components of said light beam on said path.

13. Method for stimulation of biological processes relating to cellular activity in a region of cells, comprising irradiating the region to be stimulated with light of predetermined intensity which is linearly polarized and non-coherent and having a continuous or quasi-continuous spectral distribution predominantly including wavelength components exceeding 300 nm and substantially excluding ultraviolet components and non-polarized infrared components.

14. Method of claim 13 wherein said distribution is continuous or quasi-continuous at least in the 400–700 nm range of wavelengths.

15. Method of claim 14 wherein said intensity is between 20 and 150 m W/cm$^2$ and is applied in vivo for treatment of wounds to effect healing.

16. Method of claim 13 wherein said light contains linear polarized infrared components.

17. Device for stimulating biological processes in a region of cells, comprising a housing defining a space for containing a light path, a light source in the housing for generating non-coherent light having a continuous or quasi-continuous spectral distribution of components at least in the 400–700 nm range of wavelengths, deflecting means arranged for directing the light into a beam on the path, a polarizer arranged for polarizing the light beam on the path, and filter means arranged for filtering out ultraviolet components of the light beam on the path.

18. Device for stimulating biological processes in a region of cells comprising a housing defining a space for containing a light path, a light source in the housing for generating non-coherent light of pre-determined intensity having a continuous or quasi-continuous spectral distribution, deflecting means arranged for directing the light into a beam on the path, a polarizer arranged for polarizing the light beam, and filter means arranged for filtering out components of the light beam, said light source, polarizer and filter means being constructed and arranged for providing a light beam on the path which is linearly polarized and non-coherent and having a continuous or quasi continuous spectral distribution predominantly including wavelength components exceeding 300 nm and substantially excluding ultraviolet components and non-polarized infrared components.

19. Device of claim 18 wherein said light source, polarizer and filter means are constructed and arranged for providing a light beam on the path which is linearly polarized and non-coherent and having a continuous or quasi-continuous spectral distribution at least in the 400–700 nm range of wavelengths and substantially excluding ultraviolet components and non-polarized infrared components.

20. Device of claim 18 wherein the filter means are constructed and arranged for filtering out ultraviolet components and infrared components of the light beam.

21. Device of claim 18 wherein the polarizer is constructed and arranged for polarizing infrared components of the light beam and the filter means are constructed and arranged for filtering out ultraviolet components of the light beam.

* * * * *